(12) United States Patent
Raksi

(10) Patent No.: US 8,265,364 B2
(45) Date of Patent: Sep. 11, 2012

(54) GRADIENT SEARCH INTEGRATED WITH LOCAL IMAGING IN LASER SURGICAL SYSTEMS

(75) Inventor: Ferenc Raksi, Mission Viejo, CA (US)

(73) Assignee: Alcon LenSx, Inc., Aliso Viejo, CA (US)

(*) Notice: Subject to any disclaimer, the term of this patent is extended or adjusted under 35 U.S.C. 154(b) by 435 days.

(21) Appl. No.: 12/701,409

(22) Filed: Feb. 5, 2010

(65) Prior Publication Data

US 2011/0194743 A1    Aug. 11, 2011

(51) Int. Cl.
G06K 9/00    (2006.01)
(52) U.S. Cl. ..................................... 382/128
(58) Field of Classification Search ............ 382/128
See application file for complete search history.

(56) References Cited

U.S. PATENT DOCUMENTS

| | | |
|---|---|---|
| 4,164,222 A | 8/1979 | Prokhorov et al. |
| 4,198,143 A | 4/1980 | Karasawa |
| 4,235,529 A | 11/1980 | Kawase et al. |
| 4,465,348 A | 8/1984 | Lang |
| 4,520,816 A | 6/1985 | Schachar et al. |
| 4,538,608 A | 9/1985 | L'Esperance, Jr. |
| 4,554,917 A | 11/1985 | Tagnon |
| 4,638,801 A | 1/1987 | Daly et al. |
| 4,881,808 A | 11/1989 | Bille et al. |
| 4,901,718 A | 2/1990 | Bille et al. |
| 4,907,586 A | 3/1990 | Bille et al. |
| 5,048,946 A | 9/1991 | Sklar et al. |
| 5,049,147 A | 9/1991 | Danon |
| 5,054,907 A | 10/1991 | Sklar et al. |
| 5,098,426 A | 3/1992 | Sklar et al. |
| 5,139,022 A | 8/1992 | Lempert |
| 5,246,435 A | 9/1993 | Bille et al. |
| 5,255,025 A | 10/1993 | Volk |

(Continued)

FOREIGN PATENT DOCUMENTS

WO    98/08048    2/1998
(Continued)

OTHER PUBLICATIONS

Chinn, S.R., et al., "Optical coherence tomography using a frequency-tunable optical source," *Optics Letters*, 22(5):340-342, Mar. 1997.

(Continued)

*Primary Examiner* — Gerald J. O'Connor
*Assistant Examiner* — Neha Patel
(74) *Attorney, Agent, or Firm* — Gergely T. Zimanyi

(57) ABSTRACT

Techniques and systems for gradient search are provided based on sensing or measuring at selected locations of a target object without performing full-field sensing or measuring over the entire field of the target object. Search methods are provided to include determining a coordinate of a boundary of a region in relation to a loop in a proximity of a first location, determining a direction of a gradient of the coordinate corresponding to the first location, and selecting a second location based on the determined direction. A search system can be implemented to include an imaging system to determine a coordinate of a feature of an object on a loop in a proximity of a first location, and a controller, coupled to the imaging system, to determine a direction of a gradient of the coordinate corresponding to the first location, and to select a second location based on the determined direction.

7 Claims, 9 Drawing Sheets

U.S. PATENT DOCUMENTS

| | | |
|---|---|---|
| 5,286,964 A | 2/1994 | Fountain |
| 5,321,501 A | 6/1994 | Swanson et al. |
| 5,336,215 A | 8/1994 | Hsueh et al. |
| 5,391,165 A | 2/1995 | Fountain et al. |
| 5,439,462 A | 8/1995 | Bille et al. |
| 5,493,109 A | 2/1996 | Wei et al. |
| 5,549,632 A | 8/1996 | Lai |
| 5,656,186 A | 8/1997 | Mourou et al. |
| 5,738,676 A | 4/1998 | Hammer et al. |
| 5,779,696 A | 7/1998 | Berry et al. |
| 5,795,295 A | 8/1998 | Hellmuth et al. |
| 5,954,648 A | 9/1999 | Van Der Brug |
| 5,954,711 A | 9/1999 | Ozaki et al. |
| 5,994,690 A | 11/1999 | Kulkarni et al. |
| 6,004,314 A | 12/1999 | Wei et al. |
| 6,095,648 A | 8/2000 | Birngruber et al. |
| 6,099,522 A | 8/2000 | Knopp et al. |
| 6,137,585 A | 10/2000 | Hitzenberger et al. |
| 6,254,595 B1 | 7/2001 | Juhasz et al. |
| 6,288,784 B1 | 9/2001 | Hitzenberger et al. |
| 6,314,311 B1 | 11/2001 | Williams et al. |
| 6,317,616 B1 | 11/2001 | Glossop |
| 6,337,925 B1 | 1/2002 | Cohen et al. |
| 6,377,349 B1 | 4/2002 | Fercher |
| 6,379,005 B1 | 4/2002 | Williams et al. |
| 6,451,009 B1 | 9/2002 | Dasilva et al. |
| 6,454,761 B1 | 9/2002 | Freedman |
| 6,497,701 B2 | 12/2002 | Shimmick et al. |
| 6,529,758 B2 | 3/2003 | Shahidi |
| 6,579,282 B2 | 6/2003 | Bille et al. |
| 6,623,476 B2 | 9/2003 | Juhasz et al. |
| 6,687,010 B1 | 2/2004 | Horii et al. |
| 6,730,074 B2 | 5/2004 | Bille et al. |
| 6,741,359 B2 | 5/2004 | Wei et al. |
| 6,751,033 B2 | 6/2004 | Goldstein et al. |
| 6,755,819 B1 | 6/2004 | Waelti |
| 6,763,259 B1 | 7/2004 | Hauger et al. |
| 6,769,769 B2 | 8/2004 | Podoleanu et al. |
| 6,775,007 B2 | 8/2004 | Izatt et al. |
| 6,863,667 B2 | 3/2005 | Webb et al. |
| 6,887,232 B2 | 5/2005 | Bille |
| 6,899,707 B2 | 5/2005 | Scholler et al. |
| 6,932,807 B1 | 8/2005 | Tomita et al. |
| 6,991,629 B1 | 1/2006 | Juhasz et al. |
| 6,996,905 B2 | 2/2006 | Meguro |
| 7,006,232 B2 | 2/2006 | Rollins et al. |
| 7,018,376 B2 | 3/2006 | Webb et al. |
| 7,027,233 B2 | 4/2006 | Goldstein et al. |
| 7,061,622 B2 | 6/2006 | Rollins et al. |
| 7,072,045 B2 | 7/2006 | Chen et al. |
| 7,072,047 B2 | 7/2006 | Westphal et al. |
| 7,079,254 B2 | 7/2006 | Kane et al. |
| 7,102,756 B2 | 9/2006 | Izatt et al. |
| 7,113,818 B2 | 9/2006 | Podoleanu et al. |
| 7,126,693 B2 | 10/2006 | Everett et al. |
| 7,130,054 B2 | 10/2006 | Ostrovsky et al. |
| 7,133,137 B2 | 11/2006 | Shimmick |
| 7,139,077 B2 | 11/2006 | Podoleanu et al. |
| 7,145,661 B2 | 12/2006 | Hitzenberger |
| 7,148,970 B2 | 12/2006 | de Boer |
| 7,184,148 B2 | 2/2007 | Alphonse |
| 7,207,983 B2 | 4/2007 | Hahn et al. |
| 7,248,371 B2 | 7/2007 | Chan et al. |
| 7,268,885 B2 | 9/2007 | Chan et al. |
| 7,280,221 B2 | 10/2007 | Wei |
| 7,307,733 B2 | 12/2007 | Chan et al. |
| 7,310,150 B2 | 12/2007 | Guillermo et al. |
| 7,312,876 B2 | 12/2007 | Chan et al. |
| 7,319,566 B2 | 1/2008 | Prince et al. |
| 7,330,270 B2 | 2/2008 | O'Hara et al. |
| 7,330,273 B2 | 2/2008 | Podoleanu et al. |
| 7,335,223 B2 | 2/2008 | Obrebski |
| 7,336,366 B2 | 2/2008 | Choma et al. |
| 7,342,659 B2 | 3/2008 | Horn et al. |
| 7,347,548 B2 | 3/2008 | Huang et al. |
| 7,352,444 B1 | 4/2008 | Seams et al. |
| 7,355,716 B2 | 4/2008 | de Boer et al. |
| 7,364,296 B2 | 4/2008 | Miller et al. |
| 7,365,856 B2 | 4/2008 | Everett et al. |
| 7,365,859 B2 | 4/2008 | Yun et al. |
| 7,370,966 B2 | 5/2008 | Fukuma et al. |
| 7,371,230 B2 | 5/2008 | Webb et al. |
| 7,372,578 B2 | 5/2008 | Akiba et al. |
| 7,388,672 B2 | 6/2008 | Zhou et al. |
| 7,390,089 B2 | 6/2008 | Loesel et al. |
| 7,400,410 B2 | 7/2008 | Baker et al. |
| 7,402,159 B2 | 7/2008 | Loesel et al. |
| 7,426,037 B2 | 9/2008 | Ostrovsky et al. |
| 7,433,046 B2 | 10/2008 | Everett et al. |
| 7,452,077 B2 | 11/2008 | Meyer et al. |
| 7,461,658 B2 | 12/2008 | Jones et al. |
| 7,466,423 B2 | 12/2008 | Podoleanu et al. |
| 7,477,764 B2 | 1/2009 | Haisch |
| 7,480,058 B2 | 1/2009 | Zhao et al. |
| 7,480,059 B2 | 1/2009 | Zhou et al. |
| 7,488,070 B2 | 2/2009 | Hauger et al. |
| 7,488,930 B2 | 2/2009 | Ajgaonkar et al. |
| 7,492,466 B2 | 2/2009 | Chan et al. |
| 7,503,916 B2 | 3/2009 | Shimmick |
| 7,508,525 B2 | 3/2009 | Zhou et al. |
| 7,535,577 B2 | 5/2009 | Podoleanu et al. |
| 7,537,591 B2 | 5/2009 | Feige et al. |
| 7,557,928 B2 | 7/2009 | Ueno |
| 7,575,322 B2 * | 8/2009 | Somani ........................ 351/208 |
| 7,593,559 B2 | 9/2009 | Toth et al. |
| 7,602,500 B2 | 10/2009 | Izatt et al. |
| 7,604,351 B2 | 10/2009 | Fukuma et al. |
| 7,614,744 B2 | 11/2009 | Abe |
| 7,630,083 B2 | 12/2009 | de Boer et al. |
| 7,631,970 B2 | 12/2009 | Wei |
| 7,633,627 B2 | 12/2009 | Choma et al. |
| 7,643,152 B2 | 1/2010 | de Boer et al. |
| 7,813,644 B2 | 10/2010 | Chen et al. |
| 7,898,712 B2 | 3/2011 | Adams et al. |
| 2001/0022648 A1 | 9/2001 | Lai |
| 2002/0013574 A1 | 1/2002 | Elbrecht et al. |
| 2002/0082466 A1 | 6/2002 | Han |
| 2002/0097374 A1 | 7/2002 | Payne et al. |
| 2002/0133145 A1 | 9/2002 | Gerlach et al. |
| 2003/0090674 A1 | 5/2003 | Zeylikovich et al. |
| 2004/0039378 A1 | 2/2004 | Lin |
| 2004/0059321 A1 | 3/2004 | Knopp et al. |
| 2004/0151466 A1 | 8/2004 | Crossman-Bosworth et al. |
| 2004/0243233 A1 | 12/2004 | Phillips |
| 2005/0010109 A1 | 1/2005 | Faul |
| 2005/0015120 A1 | 1/2005 | Seibel et al. |
| 2005/0021011 A1 | 1/2005 | LaHaye |
| 2005/0173817 A1 | 8/2005 | Fauver et al. |
| 2005/0192562 A1 | 9/2005 | Loesel et al. |
| 2005/0201633 A1 * | 9/2005 | Moon et al. .................... 382/268 |
| 2005/0215986 A1 | 9/2005 | Chernyak et al. |
| 2005/0284774 A1 | 12/2005 | Mordaunt |
| 2005/0286019 A1 | 12/2005 | Wiltberger et al. |
| 2005/0288745 A1 | 12/2005 | Andersen et al. |
| 2006/0020172 A1 | 1/2006 | Luerssen et al. |
| 2006/0100613 A1 | 5/2006 | McArdle et al. |
| 2006/0179992 A1 | 8/2006 | Kermani |
| 2006/0187462 A1 | 8/2006 | Srinivasan et al. |
| 2006/0195076 A1 | 8/2006 | Blumenkranz et al. |
| 2006/0206102 A1 | 9/2006 | Shimmick |
| 2007/0121069 A1 | 5/2007 | Andersen et al. |
| 2007/0126985 A1 | 6/2007 | Wiltberger et al. |
| 2007/0129709 A1 | 6/2007 | Andersen et al. |
| 2007/0129775 A1 | 6/2007 | Mordaunt et al. |
| 2007/0147730 A1 | 6/2007 | Wiltberger et al. |
| 2007/0173791 A1 | 7/2007 | Raksi |
| 2007/0173794 A1 | 7/2007 | Frey et al. |
| 2007/0173795 A1 | 7/2007 | Frey et al. |
| 2007/0185475 A1 | 8/2007 | Frey et al. |
| 2007/0189664 A1 | 8/2007 | Andersen et al. |
| 2007/0216909 A1 | 9/2007 | Everett et al. |
| 2007/0219541 A1 | 9/2007 | Kurtz |
| 2007/0230520 A1 | 10/2007 | Mordaunt et al. |
| 2007/0282313 A1 | 12/2007 | Huang et al. |
| 2007/0291277 A1 | 12/2007 | Everett et al. |
| 2008/0033406 A1 | 2/2008 | Andersen et al. |
| 2008/0049188 A1 | 2/2008 | Wiltberger et al. |

| | | | |
|---|---|---|---|
| 2008/0056610 A1* | 3/2008 | Kanda | 382/282 |
| 2008/0071254 A1 | 3/2008 | Lummis et al. | |
| 2008/0088795 A1 | 4/2008 | Goldstein et al. | |
| 2008/0100612 A1 | 5/2008 | Dastmalchi et al. | |
| 2008/0281303 A1 | 11/2008 | Culbertson et al. | |
| 2008/0281413 A1 | 11/2008 | Culbertson et al. | |
| 2008/0319427 A1 | 12/2008 | Palanker | |
| 2009/0012507 A1 | 1/2009 | Culbertson et al. | |
| 2009/0088734 A1 | 4/2009 | Mordaunt | |
| 2009/0125005 A1 | 5/2009 | Chernyak et al. | |
| 2009/0131921 A1 | 5/2009 | Kurtz et al. | |
| 2009/0157062 A1 | 6/2009 | Hauger et al. | |
| 2009/0168017 A1 | 7/2009 | O Hara et al. | |
| 2009/0268161 A1 | 10/2009 | Hart et al. | |
| 2010/0004641 A1* | 1/2010 | Frey et al. | 606/4 |
| 2010/0004643 A1 | 1/2010 | Frey et al. | |
| 2010/0007848 A1 | 1/2010 | Murata | |
| 2010/0022994 A1 | 1/2010 | Frey et al. | |
| 2010/0022995 A1 | 1/2010 | Frey et al. | |
| 2010/0022996 A1 | 1/2010 | Frey et al. | |
| 2010/0042079 A1 | 2/2010 | Frey et al. | |
| 2010/0110377 A1 | 5/2010 | Maloca et al. | |
| 2010/0324543 A1 | 12/2010 | Kurtz et al. | |
| 2011/0022036 A1 | 1/2011 | Frey et al. | |

FOREIGN PATENT DOCUMENTS

| | | |
|---|---|---|
| WO | 9808048 A1 | 2/1998 |
| WO | 2006074469 | 7/2006 |
| WO | 2007130411 | 11/2007 |

OTHER PUBLICATIONS

Huber, R., et al., "Three-dimensional and C-mode OCT imaging with a compact, frequency swept laser source at 1300 nm," *Optics Express*, 13(26):10523-10538, Dec. 2005.

Massow, O., et al., "Femtosecond laser microsurgery system controlled by optical coherence tomography," *Proceedings of the SPIE—Commercial and Biomedical Applications of Ultrafast Lasers VIII*, vol. 6881, pp. 688106(1)-688106(6), Mar. 2008.

Massow, O., et al., "Optical coherence tomography controlled femtosecond laser microsurgery system," *Proceedings of the SPIE—Optical Coherence Tomography and Coherence Techniques III*, vol. 6627, pp. 662717(1)-662717(6), Aug. 2007.

Ohmi, M., et al., "In-situ Observation of Tissue Laser Ablation Using Optical Coherence Tomography," *Optical and Quantum Electronics*, 37(13-15):1175-1183, Dec. 2005.

Sarunic, M., et al., "Imaging the Ocular Anterior Segment With Real-Time, Full-Range Fourier-Domain Optical Coherence Tomography," *Archives of Ophthalmology*, 126(4):537-542, Apr. 2008.

Sarunic, M., et al., "Instantaneous complex conjugate resolved spectral domain and swept-source OCT using 3x3 fiber couplers," *Optics Express*, 13(3):957-967, Feb. 2005.

Sarunic, M. et al. "Real-time quadrature projection complex conjugate resolved Fourier domain optical ical coherence tomography," *Optics Letters*, 31(16):2426-2428, Aug. 2006.

Swanson, et al., "Method and Apparatus for Optical Imaging with Means for Controlling the Longitudinal Range of the Sample," U.S. Re-exam Patent Application No. 90/006,816, filed Oct. 20, 2003.

Tao, Y., et al., "High-speed complex conjugate resolved retinal spectral domain optical coherence tomography using sinusoidal phase modulation," *Optics Letters*, 32(20):2918-2920, Oct. 2007.

Yun, S.H., et al., "Wavelength-swept fiber laser with frequency shifted feedback and resonantly swept intra-cavity acoustooptic tunable filter," *IEEE Journal of Selected Topics in Quantum Electronics*, 3(4):1087-1096, Aug. 1997.

International Search Report and Written Opinion dated Mar. 12, 2009 for International Application No. PCT/US2008/075511, filed Sep. 5, 2008 (9 pages).

European Patent Office, European Patent Application No. 10191057.8, in European Search Report, mailed Mar. 16, 2011, to be published by the USPTO, 3 pages.

Arimoto et al., "Imaging Properties of Axicon in a Scanning Optical System," Nov. 1, 1992, Applied Optics, 31(31): 6652-6657, 5 pages.

Birngruber et al., "In-Vivo Imaging of the Development of Linear and Non-Linear Retinal Laser Effects Using Optical Coherence Tomography in Con-elation with Histopathological Findings," 1995, Proc. SPIE 2391:21-27, 7 pages.

Stern et al., "Femtosecond Optical Ranging of Corneal Incision Depth," Jan. 1989, Investigative Ophthalmology & Visual Science, 30(1):99-104, 6 pages.

Fercher et al., "Eye-Length Measurement by Interferometry With Partially Coherent Light," Mar. 1988, Optics Letters, 13(3):186-188, 3 pages.

Fercher et al., "Measurement of Intraocular Distances by Backscattering Spectral Interferometry," May 15, 1995, Optics Comm. 117:43-48, 6 pages.

Wojtkowski et al., "In Vivo Human Retinal Imaging by Fourier Domain Optical Coherence Tomography," Jul. 2002, Journal of Biomedical Optics 7(3):457-463, 7 pages.

Izatt et al., Micron-Resolution Biomedical Imaging With Optical Coherence Tomography, Oct. 1993, Optics & Photonics News, pp. 14-19, 6 pages.

U.S. Appl. No. 90/006,816, filed Feb. 27, 2007, Swanson et al.

PCT International Search Report and Written Opinion dated Feb. 9, 2012 for International Application Serial No. PCT/US2011/040223.

Hee et al.; "Femtosecond transillumination optical coherence tomography"; Optics Letters; vol. 18; No. 12; pp. 950-952 (Jun. 1993).

Kamensky et al.; "In situ monitoring of the middle IR laser ablation of a cataract-suffered human lens by optical coherent tomography"; Proc. SPIE; 2930: 222-229 (1996).

Kamensky et al.; "Monitoring and animation of laser ablation process in cataracted eye lens using coherence IDS 41 tomography"; Proc. SPIE; 2981: 94-102 (1997).

Ostaszewski et al.; "Risley prism beam pointer"; Proc. of SPIE; vol. 6304; 630406-1 through 630406-10.

PCT International Search Report for International Application Serial No. PCT/US2010/056701 mailed Aug. 24, 2011.

Swanson et al.; "In vivo retinal imaging by optical coherence tomography"; Optics Letters; vol. 18; No. 21; pp. 1864-1866 (Nov. 1993).

Kim, Tae Hoon, Authorized Officer, Korean Intellectual Property Office, PCT International Application No. PCT/US2011/023710, in International Search Report, mailed Aug. 24, 2011, 8 pages.

Kim, Tae Hoon, Authorized Officer, Korean Intellectual Property Office, PCT International Application No. PCT/US2011/025332, in International Search Report, mailed Sep. 16, 2011, 8 pages.

* cited by examiner

GRADIENT SEARCH INTEGRATED WITH LOCAL IMAGING IN LASER SURGICAL SYSTEMS

TECHNICAL FIELD

This patent document relates to gradient search techniques for various applications, including ophthalmic surgical applications.

BACKGROUND

There are many methods to image objects or portions of objects for a wide variety of purposes, including manufacturing, diagnostics, quality control, surgical applications and many more. Optical Coherence Tomography (OCT) is one of the many methods to create three dimensional images and extract structural information of materials. This is usually done by scanning an optical beam over a target region or surface and then analyzing the spatial, spectral and temporal characteristics of the scattered and returned light. Detailed imaging information can be obtained by scanning along a two or three dimensional grid pattern of a sufficiently high spatial density.

SUMMARY

For many applications, however, there is no need to or it is not advantageous to create a complete image of an entire region or surface. One of these applications is the task to find specific points of an imaged surface or region. These specific points can be extrema of the imaged surface, features of the imaged object, or boundary points or edges of the object. This document discloses technique and systems for gradient search based on sensing or measuring at selected locations of a target object without performing the full-field sensing or measuring over the entire field of the target object.

Ophthalmic surgeries often encounter situations where the surgical procedure can be directed relative to a reference point, such as the apex of the cornea. In cataract procedures, the reference points can be the apex of the anterior or posterior surface of the lens, or its hardened nucleus. Reference points can be identified by, e.g., first scanning the target region with an imaging beam by a series of planar B, radial or cylindrical OCT scans. The scanned data can be analyzed and used to compose a full three dimensional image of the targeted region, surface or object. These image data then can be stored. Subsequently, search algorithms can be used on the stored image data to identify the maxima or minima of interest.

However, imaging the entire target region, especially with high density scanning to ensure good resolution, is unnecessarily wasteful as it stores lots of data points which are eventually not used. Further, taking these large amounts of data is time consuming and thus the process is slow. Thus, in applications where time is at a premium, these applications are at a disadvantage.

To improve the efficiency of such imaging processes, for example, a search method for surgical imaging can include the steps of determining a coordinate of a boundary of a region in relation to a loop in a proximity of a first location, determining a direction of a gradient of the coordinate corresponding to the first location, and selecting a second location based on the determined direction.

In embodiments, the determined coordinate is one of a height, a depth, a z coordinate, and a coordinate along a reference line.

In embodiments, the loop is one of a closed loop, a loop in a plane, a loop on a predetermined surface, an ellipse and a circle.

In embodiments, the first location is one of a location in a plane transverse to an axis, a location in a plane transverse to the determined coordinate, a location in an (x,y) plane, a location in a radial coordinate system, and a coordinate on a predetermined surface.

In embodiments, the coordinate is determined by one of an optical coherence tomography, a depth measurement technology, an optical measurement, and a sensing technology of a merit function.

In embodiments, the determining a direction of a gradient step includes determining at least one of a direction of a maximum of the coordinate along the loop and a direction of a minimum of the coordinate along the loop, and determining the direction of the gradient based on at least one of the direction of the maximum and the direction of the minimum.

In embodiments, the selecting a second location step includes selecting the second location by shifting the first location by an increment vector, a direction of the increment vector being approximately parallel to the direction of the gradient.

In embodiments, the first location is retained when a magnitude of the gradient is smaller than an iteration-stop value.

In embodiments, the determining a coordinate of a boundary of a region in relation to a loop in the proximity of a first location step includes identifying rays around the first location, and determining the coordinate at ray-points.

In embodiments, the determining a direction of a gradient of the coordinate around the loop step includes determining a rate of change of the coordinate along the rays, selecting the ray along which the rate of change is maximum, and identifying a direction of the selected ray as the direction of the gradient, and the rate of change along the selected ray as the magnitude of the gradient.

In embodiments, the method includes shifting the first location by a shake-up vector having at least one of a direction making a non-zero angle with the direction of the gradient, or a magnitude substantially different from the magnitude of the gradient.

In embodiments, the search method is performed without determining the coordinate of the boundary of the region in one of a volume, along parallel lines, in a two dimensional raster, on a grid, and in a raster on a surface.

In embodiments, the boundary of the region is an ophthalmic layer of one of a cornea, a lens, and a cataract, the coordinate is a depth of the ophthalmic layer, and the search method includes determining an extremum of the depth of the ophthalmic layer.

In embodiments, the search method is capable of determining the extremum of the ophthalmic layer faster than one of 10 msec, 100 msec, 1 sec and 10 sec.

In embodiments, a search system includes an imaging system, to determine a coordinate of a feature of an object on a loop in a proximity of a first location, and a controller, coupled to the imaging system, to determine a direction of a gradient of the coordinate corresponding to the first location, and to select a second location based on the determined direction.

In embodiments, the imaging system includes a scanner, to scan an imaging beam, and an image acquisition sub-system, to receive and to pre-process a returned imaging beam.

In embodiments, the imaging system is one of an optical coherence tomography system, a depth measurement system, an optical sensing system, and a sensing system of a merit function.

In embodiments, the controller is configured to determine at least one of a location of a maximum of the coordinate along the loop and a location of a minimum of the coordinate along the loop, and to determine the direction of the gradient by relating any two of the first location, the location of the maximum and the location of the minimum.

In embodiments, the controller is configured to select the second location by shifting the first location by an increment vector, a direction of the increment vector being essentially parallel to the direction of the gradient.

In embodiments, the controller is configured to retain the first location when a magnitude of the gradient is smaller than an iteration-stop value.

In embodiments, the imaging system is an ophthalmic coherence tomography system, the imaged object is an ophthalmic layer of one of a cornea, a lens, and a cataract, the coordinate is a depth of the ophthalmic layer, and the controller is configured to determine an extremum of the depth of the ophthalmic layer.

In embodiments, the search system is configured to determine the extremum of the ophthalmic layer faster than one of 10 msec, 100 msec, 1 sec and 10 sec.

In embodiments, a search method for surgical imaging includes the steps of: performing a local search of a merit function of an imaged region in a proximity of a first location, determining a preferred direction based on the local search, and selecting a second location based on the preferred direction.

In embodiments, the performing the local search step includes surgical imaging by one of an optical coherence tomography, a depth measurement technology, an optical sensing technology and a sensing technology of the merit function.

In embodiments, the performing the local search step includes determining one of a height, a depth, a z coordinate, a coordinate along a line of reference, an optical density, and an optical scattering intensity.

In embodiments, the performing the local search step includes determining the merit function along one of a closed loop, a loop in a plane, a loop on a predetermined surface, an ellipse, a circle, an essentially closed surface, an ellipsoid, and a sphere.

In embodiments, the performing the local search step includes determining the merit function along local rays.

In embodiments, the determining a preferred direction step includes determining a direction of a gradient of the merit function.

In embodiments, the determining the direction of the gradient step includes determining at least one of a location of a maximum of the merit function on an essentially closed surface or loop in the proximity of the first location, and a location of a minimum of the merit function on the essentially closed surface or loop in the proximity of the first location and determining the direction of the gradient by relating any two of the first location, the location of the maximum and the location of the minimum.

In embodiments, the selecting a second location step includes selecting the second location by shifting the first location by an increment vector, a direction of the increment vector being essentially parallel to the direction of the gradient.

In embodiments, the method includes retaining the first location when the magnitude of the gradient is smaller than an iteration-stop value.

In embodiments, the search method is performed without determining the merit function in one of a volume, along parallel lines, on aligned surfaces, in a two dimensional raster, and in a three dimensional raster.

In an other example, a method for searching a gradient of a function over a target object is described to include selecting a first location of the target object; performing a sensing or measuring operation at the first location to obtain a respective value of the function; selecting a first loop having multiple first loop locations of the target object that are different from the first location; and performing a sensing or measuring operation at the multiple first loop locations of the first loop, without performing the sensing or measuring operation at other locations, to obtain values of the function at the respective multiple first loop locations. One of the multiple first loop locations that has the maximum or minimum value for the function among the multiple first locations is selected. The first location and the selected first loop location that has the maximum or minimum value for the function among the multiple first loop locations, and corresponding values of the function are used to determine a first gradient between the first location and the selected first loop location. Next, a second location of the target object is selected along a direction of the first gradient and a sensing or measuring operation at the second location is performed to obtain a respective value of the function. A second loop having multiple second loop locations of the target object that are different from the second location is selected and a sensing or measuring operation at the multiple second loop locations, without performing the sensing or measuring operation at other locations, is performed to obtain values of the function at the respective multiple second loop locations. One of the multiple second loop locations that has the maximum or minimum value for the function among the multiple second locations is selected and the second location and the selected second loop location that has the maximum or minimum value for the function among the multiple second t loop locations, and corresponding values of the function are used to determine a second gradient between the second location and the selected second loop location.

The above and other aspects of the techniques and systems for gradient search based on sensing or measuring at selected locations of a target object are described in detail in the drawings, the description and the claims.

DETAILED DESCRIPTION

The challenge of finding the coordinates $\vec{x}_{ext}$ of the extrema of a function $F_{ext}(\vec{x}_{ext})$ arises in various applications, where $\vec{x}$ is a position vector in a space of two or more dimensions, such as a position vector on an object surface or in an object volume of interest. The basis of the gradient, or steepest descent or ascent method is that if the function $F(\vec{x})$ is real-valued and is differentiable in a neighborhood of a location $\vec{a}$, then $F(\vec{x})$ varies fastest in the direction of the gradient vector of F at $\vec{a}$, $\vec{\nabla}F(\vec{a})$. Therefore, the $\vec{x}_{max}$ location of the maximum $F_{max}(\vec{x}_{max})$ can be found efficiently by repeatedly updating an initial location in the direction of the gradient vector, corresponding to each update. Similarly, the $\vec{x}_{min}$ location of the minimum $F_{min}(\vec{x}_{min})$ can be found efficiently by repeatedly updating an initial location in the direction opposite to the gradient vector, corresponding to each update.

In an example of the maximum-searching algorithm the position vector is moved or updated from $\vec{x}_1$ to $\vec{x}_2$ according to the relation:

$$\vec{x}_2 = \vec{x}_1 + \gamma \vec{\nabla} F(\vec{x}_1) \qquad (1)$$

For a sufficiently small $\gamma>0$, the update increases the value of the function $F(\vec{x})$: $F(\vec{x}_1) \leq F(\vec{x}_2)$. Repeatedly updating the location $\vec{x}$ along the corresponding gradient vectors is therefore an iterative process which generates a sequence of locations $\vec{x}(1), \vec{x}(2), \ldots \vec{x}(n)$ with the iterative relation:

$$\vec{x}(n+1) = \vec{x}(n) + \gamma(n) \vec{\nabla} F(\vec{x}(n)) \qquad (2)$$

The above iterative relation generates a corresponding sequence of growing values of the function $F(\vec{x})$:

$$F(\vec{x}(1)) \leq F(\vec{x}(2)) \ldots \leq F(\vec{x}(n)) \qquad (3)$$

These values converge to a maximum of $F(\vec{x})$, at least locally. In a generic formulation, the starting coordinate $\vec{x}(1)$ can be chosen randomly, or based on some preexisting knowledge or on a guess of the location of the maximum. The step size, controlled by $\gamma(n)$, can be a constant, or a variable that depends on n, chosen according to some suitable condition.

The analogous minimum-searching algorithm can update the location $\vec{x}$ according to:

$$\vec{x}(n+1) = \vec{x}(n) - \gamma(n) \vec{\nabla} F(\vec{x}(n)) \qquad (4)$$

and proceed analogously otherwise.

Figure 1A:
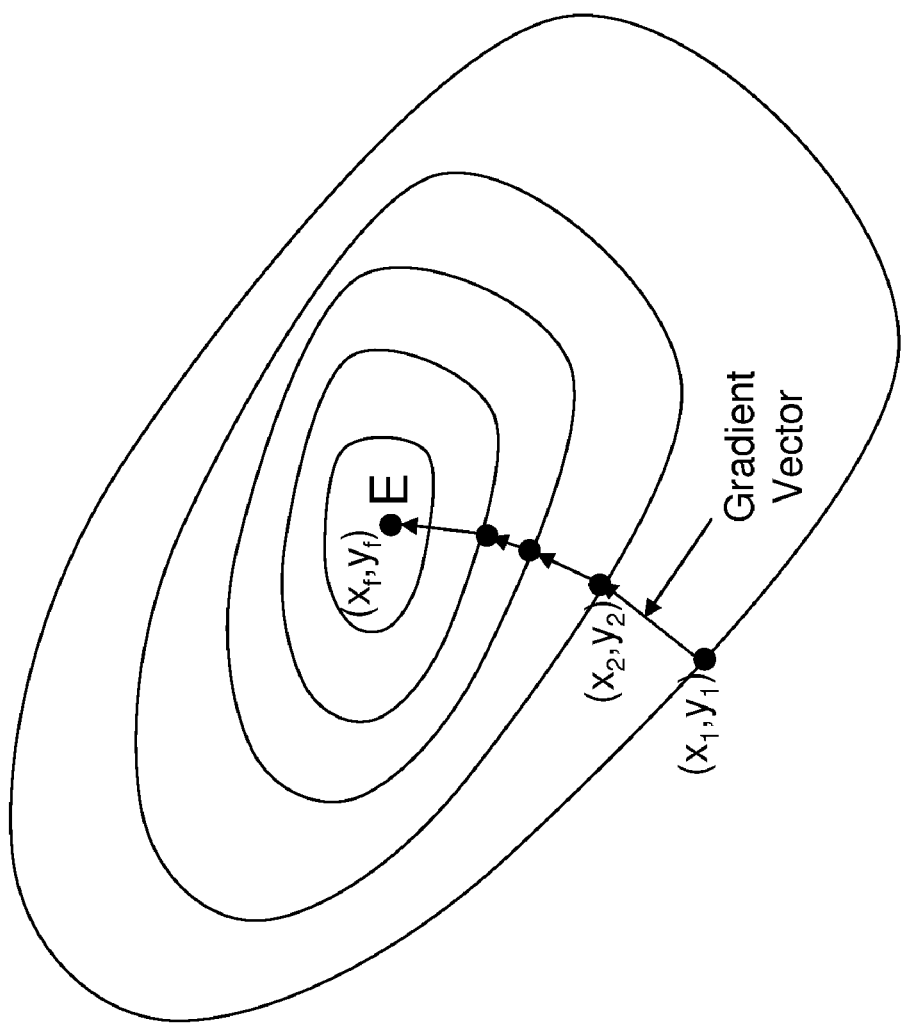
FIG. 1A illustrates the principle of the gradient search algorithm.

FIG. 1A illustrates a gradient search algorithm. Here $\vec{x}$ is a two dimensional location (x,y) and $F(\vec{x})$ is a scalar function. The closed loops are iso-value lines, or contour lines, connecting points where $F(\vec{x})$ assumes the same value. The set of embedded closed iso-value lines enclose an extremum E which can be either a maximum or a minimum.

Referring to the maximum-searching algorithm, the gradient search algorithm can use a step-vector, or update-vector, which updates the initial location (x1,y1) with a vector parallel to the gradient vector at that point: $\vec{\nabla} F(x1,y1)$, resulting in the updated location (x2,y2), as shown in Eq. (2). The length of the update-vector is controlled by $\gamma(n)$. FIG. 1A shows that the direction of the gradient vector at each location is orthogonal to the contour line going through the same location.

Repeated updating of the location through the sequence (x1,y1), (x2,y2), ... (xn,yn) generates a sequence of increasing function values:

$$F(x1,y1) \leq F(x2,y2) \ldots \leq F(xn,yn) \qquad (5)$$

The gradient search method typically monitors the sequence of function values. When the increase of the function values falls below a threshold value, the algorithm presumably reached a close proximity of maximum of the function. The algorithm is then typically stopped and the location of this final point $\vec{x}_{max} = (xf,yf)$, as well as the corresponding maximum value of the function $F_{max}(\vec{x}_{max})$ are reported as the result of the algorithm.

Some algorithms can involve a step of shortening the length of the update-vector through decreasing $\gamma(n)$ when the increase of the function falls below the threshold value, to avoid overshooting, or the search entering into a non-convergent cycle.

The above described gradient search algorithm can be applied and implemented in several different ways. The function $F(\vec{x})$ can be a wide variety of quantities, including, for example, a height, depth, temperature, optical or electromagnetic absorption, a merit function for a search and a scalar function in various applications. Accordingly, the location $\vec{x}$ can be a multidimensional vector, including spatial coordinates in two or three dimensions, in a relative or fixed coordinate system. In a generic search for optimizing a merit function, the location can be an appropriate state vector.

The values of the wide variety of functions, $F(\vec{x})$, can be acquired by a wide variety of suitable methods, often involving sensing or measuring operations on a target surface or within a target volume of an object. Examples of sensing or measuring operations for obtaining values of the function $F(\vec{x})$ include: measuring the height or depth of a target object surface, a thickness of a target object tissue, volume or region by mechanical sensors or by optical imaging; measuring a refractive property, a density, or an other optical property; and measuring the temperature distribution by temperature sensors, e.g., direct contact temperature sensors, or by infrared sensors operating from a distance. The sensed values of the function $F(\vec{x})$ can then be used to perform the rest of the gradient search method, as described above.

Figure 1B:
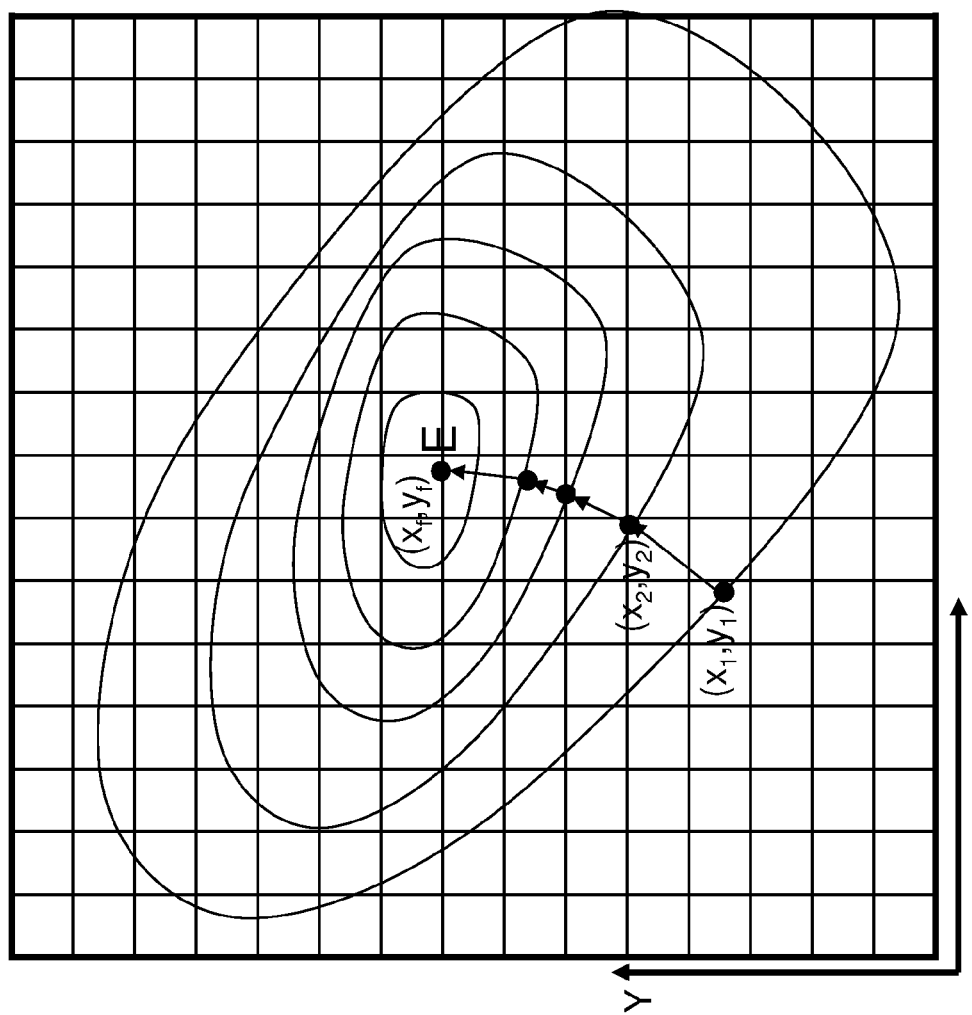
FIG. 1B illustrates a grid-scanning pattern used for imaging.

Many gradient search techniques perform a full-field sensing or measuring operation to obtain the values of the function $F(\vec{x})$ for the entire target area or volume of an object. As an example, FIG. 1B illustrates that some methods can perform the gradient search on a grid-scanned dataset. The scanning can be performed on an (x,y)-grid, the scanning data stored, and the gradient search algorithm performed subsequently on the stored scanning data. FIG. 1B shows a sparse grid for clarity. In many applications, a much denser grid can be applied to reach the desired precision.

Performing the gradient search on the full-field grid-scanned data may have drawbacks and limitations in certain applications. For example, sensing the values of the function $F(\vec{x})$ of the entire target area or volume of the object can acquire a large number of data points which are often not used for the subsequent gradient search. As a result, such grid-scanning can be wasteful of the processing time. For another example, the grid-scanning method can be slow, since acquiring the unused scanned data takes time and this slow process can undermine the applicability of this method for time sensitive applications which require finding the extremum in a short time.

Search techniques described in this document can be implemented in ways that address these and other technical issues and challenges by an integrated gradient search which senses the function $F(\vec{x})$ only locally, determines the gradient on this small set of locally sensed values and updates the location x based on the determined gradient. Such an integrated technique has a built-in intelligence to select only a limited number of locations to perform the sensing or measuring the values of the function $F(\vec{x})$ without performing the full-field sensing or measuring over the entire field of the target object area or volume. The selection of the limited number of locations to perform the sensing or measuring operation reduces the processing time and uses the system resources efficiently by only capturing and storing data that is relevant to the gradient search. This integration allows the scanning for the sensing or measuring operation to be local only without being performed globally in the entire field of the target object area or volume of interest. Since these search algorithms involve only local scans, they can be considerably faster than scanning the target over entire grids and thus reduce the scanning and computational effort and time.

Such implementations can be useful for imaging applications which do not require the full two or three dimensional grid-scanned information about the imaged object, but instead they are directed towards determining only certain features, for example the extrema of the spatial extent of the object or the location of a maximum of the optical absorption, or any other reference point.

Some embodiments of this integrated gradient search method can be implemented in ophthalmic applications, where this integrated gradient search method can be useful for several different functionalities:

1) Implementations can be used to find spatial extrema of boundaries of tissues in the eye. These extrema can be used as reference points for positioning and directing surgical procedures. Reference points can include, for example, an apex of a cornea or an apex of an anterior or posterior surface of a crystalline lens or a retina. Other characteristics, such as a thickness of the lens, or an axial length of the eye can be derived from these measurements.

2) Implementations can be used to locate extrema of a cataract in the lens of the eye. The cataract may occupy only a portion of the lens, associated with the most hardened region of the nucleus.

3) Implementations can be used to find an extremum of ophthalmic regions to guide surgical procedures where time is of essence. In ophthalmic procedures patients often lose their ability to keep their eyes motionless after 90-120 seconds. Therefore, fast searching for reference points to guide the ophthalmic surgery can be quite important for a timely completion of the ophthalmic surgery.

While below the implementations are explained primarily in surgical context, embodiments can be also used in the context of any of the applications listed above, further including any diagnostic procedures or manufacturing process as well, where any kind of imaging process is used, such as optical coherence tomography, or OCT.

Figure 2:
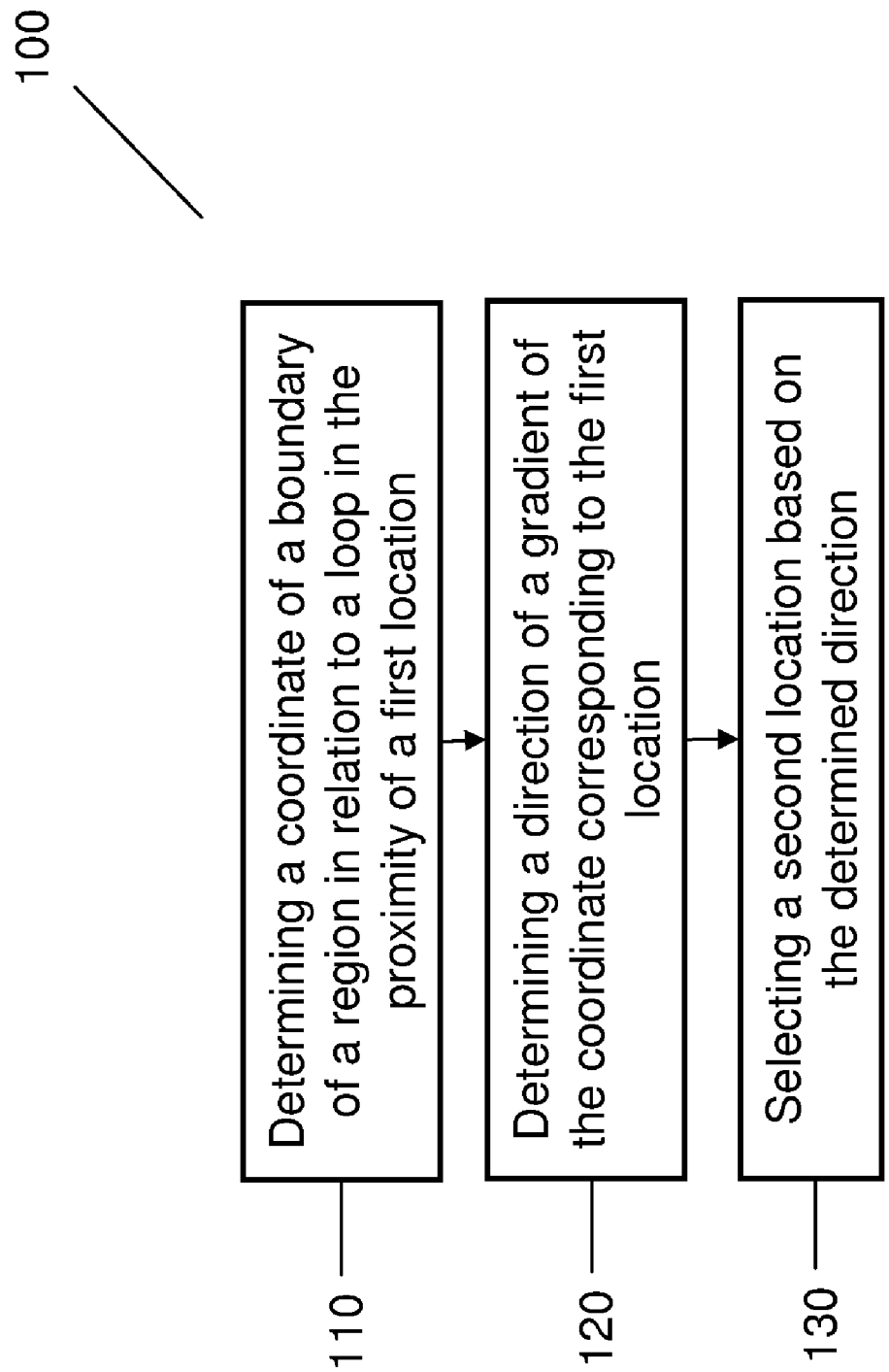
FIG. 2 illustrates an embodiment of a gradient search integrated with local imaging method 100.

FIG. 2 shows an embodiment of the Gradient Search Integrated with Local Imaging (GSILI) method 100. The GSILI method 100 first determines a coordinate of a boundary of a region in relation to a loop in the proximity of a first location in step 110. Next, the method 100 determines a direction of a gradient of the coordinate corresponding to the first location in step 120. Finally, a second location is selected based on the determined direction in step 130.

In implementing the method 100, the boundary of the region can be a surface of an imaged three dimensional object. The boundary can be defined by expressing e.g. the z coordinate of the surface as a function of the corresponding (x,y) location. In the language of the above general description, this z coordinate or height is the $F(\vec{x})$ function whose extrema are sought: $F(\vec{x})=z(x, y)$.

The first location can be a location in a plane transverse to an axis, a location in a plane transverse to the determined coordinate, a location in an (x,y) plane, a location in a radial coordinate system, and a location on a predetermined surface. The above described Cartesian coordinate system is but one example where the (x,y) coordinates define the first location and the z coordinate is the determined coordinate.

In step 110 a first loop can be selected in relation to the first location. The first loop can be centered around the first location, or can be in the proximity of the first location. Next, the values of the function $F(\vec{x})$ can be sensed or measured at a set of locations along a first loop. Specific examples for implementing the method 100 are described below in terms of an algorithm searching for the extrema of a coordinate which can be a height, a depth, a z coordinate, and a coordinate along a reference line. The GSILI method 100 can be implemented for various other $F(\vec{x})$ functions, including an optical property, a merit function, and a scalar function.

After the sensing or measuring operation is performed on the first loop around the first location, some implementations of method 100 select the loop location on the first loop that has the maximum or minimum value of the $F(\vec{x})$ function. A first gradient can be determined based on the values of the $F(\vec{x})$ function at this selected loop location and the first location. Along this first gradient, a second location can be selected within the target area or volume of the object, in effect "updating the first location". The cycle can be completed by selecting a second loop in the proximity of the second location.

The new cycle starts by sensing or measuring the values of the function $F(\vec{x})$ along the second loop. Next, the loop location on the second loop is selected that has the maximum or minimum value of the $F(\vec{x})$ function. A second gradient can be determined based on the values of the $F(\vec{x})$ function at this selected loop location and the second location. Along this second gradient, a third location within the target area or volume of the object can be selected and the second location updated to this third location. The cycles of the above process can be repeated until the search for the maximum or minimum is completed.

In the above process, the use of a loop in connection with a location provides the local intelligence for selecting the next location for the gradient search. The sensing or measuring operation is performed locally along the loop rather than globally at all locations on the grid within the entire target area or volume of the object. Therefore, the local sensing or measuring operation and the updating of the location according to the local gradient are integrated and interleaved during the gradient search. These steps and their various implementations will be now described in more detail below.

The GSILI method 100 can search for the extrema of a boundary of the imaged object. An ophthalmic example is the apex of a section of the eye, such as the cornea. Another example is the apex of the hardened center of a nucleus of the lens.

Figure 3A:
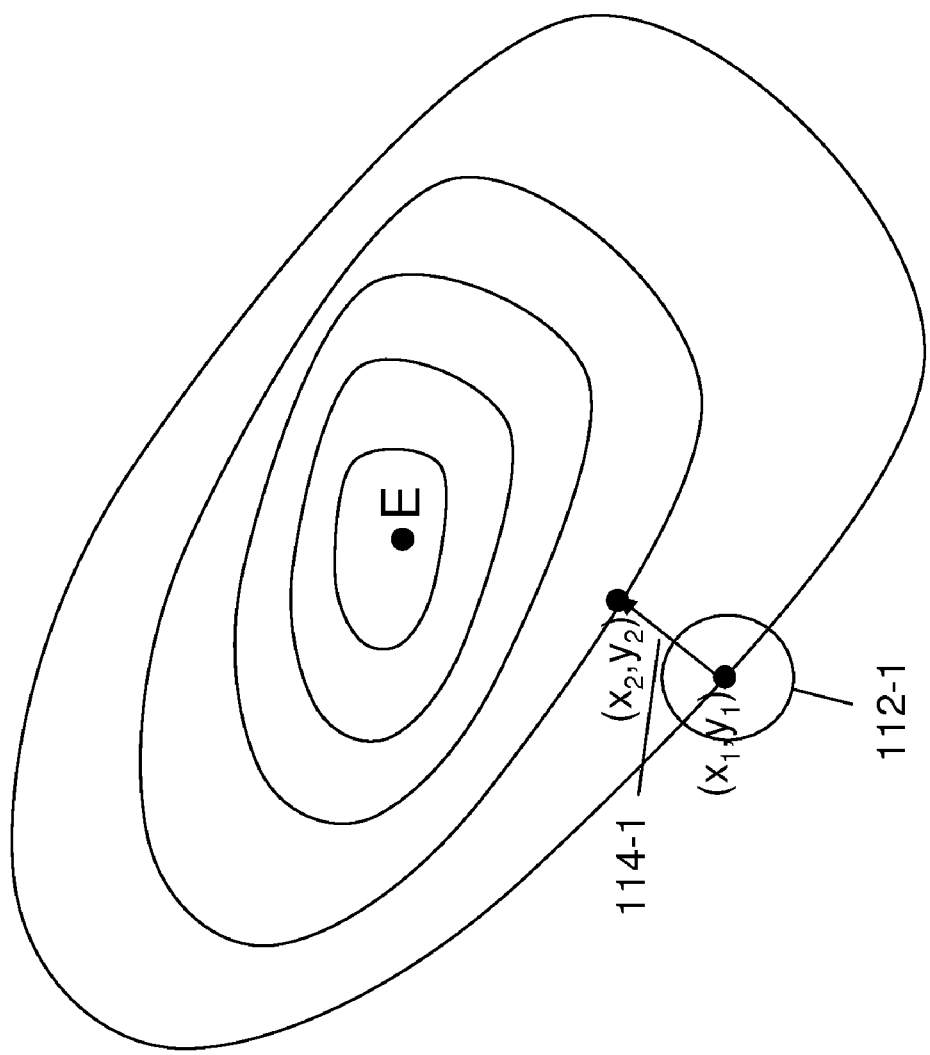
FIGS. 3A-B illustrate the local search step in association with a loop corresponding to a first location.

FIG. 3A illustrates that in step 110 the coordinate, such as the z coordinate of the boundary of the imaged object, can be determined on a loop 112-1 in the proximity of a starting point (x1,y1). In an example the loop 112-1 can be centered around the starting point (x1,y1). In other examples, the starting point (x1,y1) can be off the center of the loop 112-1, or even outside the loop, in a predetermined relation with it. The loop 112-1 can be a closed loop, a loop in a plane, a loop on a predetermined surface, an ellipse and a circle. In some cases there can be one or more discontinuities along the loop 112-1.

In some embodiments of the step 110 the values of the coordinate can be determined not continuously, but only at a set of points along the loop 112. The points can be located densely or with some separation along the loop.

In step 110 the coordinate can be determined by an optical coherence tomography (OCT), a depth measurement technology and a sensing technology of a merit function.

In an example, a focal spot of an imaging beam can be scanned along the loop 112-1 by a scanner. The loop can lie in the (x,y) plane, centered at the point (x1,y1). The coordinate, such as the $z=z(x_1,y_1)$ depth of the boundary of the imaged object, can be determined by sensing the imaging beam returned from the boundary by an image acquisition system. The z depth coordinate can be sensed essentially continuously, or at a set of points $(x_1,y_1)$ as the focal spot of an imaging beam is scanned along the loop 122-1.

The surface $z=z(x,y)$ can be distinguished e.g. by the optical scattering being measurably different on the two sides of the surface. Any optical imaging technology can be used for determining the coordinate, measuring reflectivity, scattering, transmittivity or absorptivity. The measurement can utilize any part of the electromagnetic spectrum, including the infrared and ultraviolet portions.

The overall application of the GSILI method 100 can be started by selecting a starting location (x1,y1). The starting location can be selected randomly, or by using some predetermined information, e.g. a result of a prior imaging, facts from general knowledge, or an educated guess.

Figure 3B:
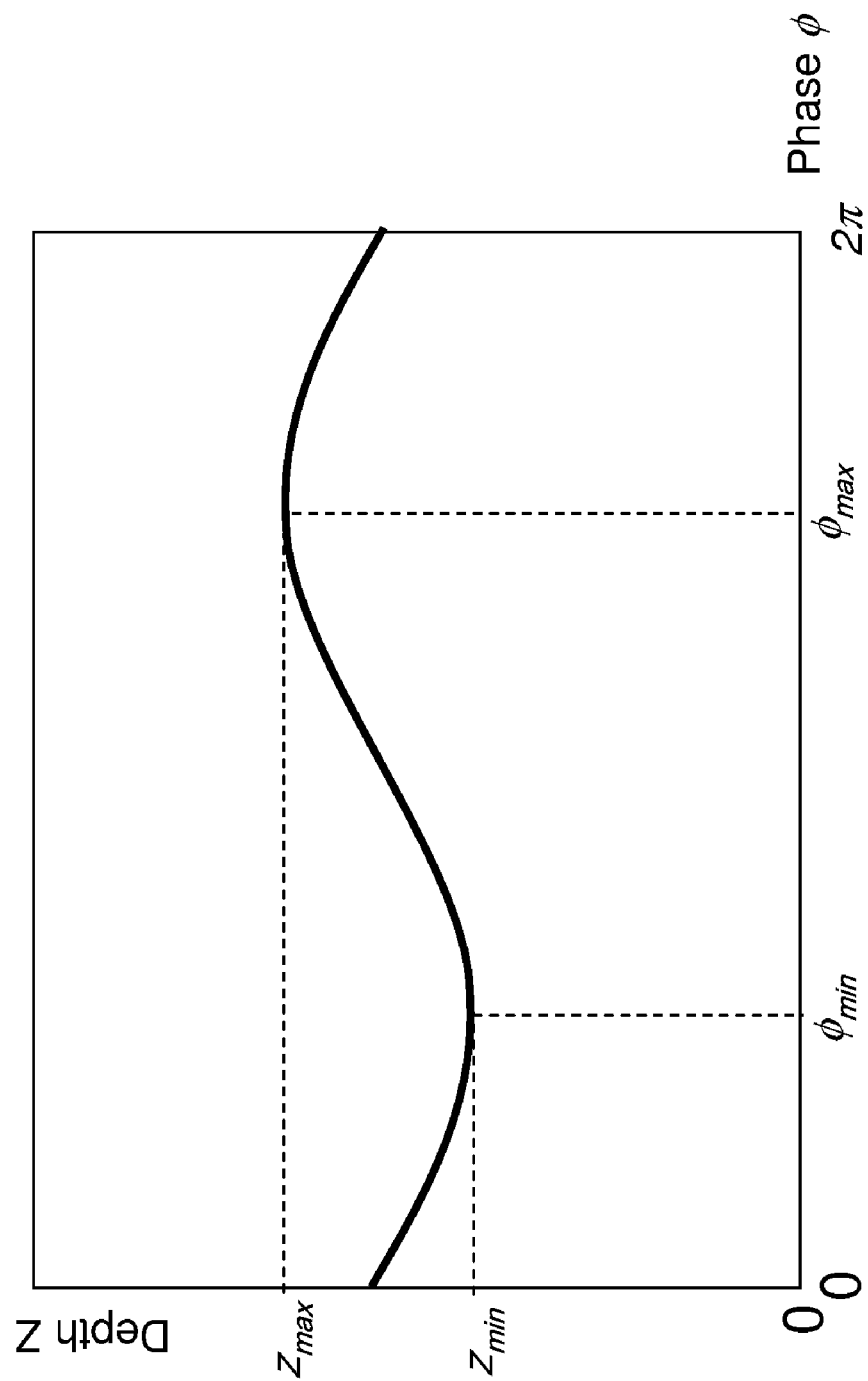

FIG. 3B illustrates a possible result of step 110: the value of the coordinate determined along the loop, parametrized by the polar or azimuth angle $\phi$. Sometimes this type of scanning is called creating a circular B-scan.

In step 120 a direction of a gradient can be determined by recalling that the direction of the gradient at a location is essentially the direction of the maximum change of the coordinate at that location. Thus, the direction of the gradient can be determined by determining at least one of a maximum of the coordinate $z_{max}$ along the loop and its direction relative to the center of the loop, characterized by the corresponding azimuth or polar angle $\phi_{max}$, and a minimum of the coordinate $z_{min}$, along the loop and its direction relative to the center of the loop, characterized by the corresponding azimuth or polar angle $\phi_{min}$. From these values the direction of the gradient can be determined based on at least one of the directions of the maximum and the minimum. The direction of the gradient can be identified by different methods, e.g. as:

(i) the direction of the maximum, characterized by a vector originating at (x1,y1) and pointing in the direction of the azimuth angle $\phi_{max}$; or by (ii) the direction of the minimum, characterized by a vector parallel to the direction of the azimuth angle $\phi_{min}$, pointing towards (x1,y1); or by (iii) directly connecting the points along the loop corresponding to $\phi_{max}$ and $\phi_{min}$.

The magnitude of the gradient in the above three cases (i)-(iii) measured on a loop of radius r can be approximated by:

$$|\vec{\nabla} z(x1,y1)| \approx (z_{max}-z(x1,y1))/r; \text{ or} \qquad (i)$$

$$|\vec{\nabla} z(x1,y1)| \approx (z(x1,y1)-z_{min})/r; \text{ or} \qquad (ii)$$

$$|\vec{\nabla} z(x1,y1)| (z_{max}-z_{min})/2r). \qquad (iii)$$

Since the gradient is a numerical derivative, or at least a finite differential of discrete data, typically it can have undesirably poor precision, or equivalently, high noise. To remedy this problem, the numerical noise in the values of the polar angles $\phi_{max}$ and $\phi_{min}$ can be reduced by averaging or curve fitting the polar angle $\phi$ along the loop. The numerical noise in the magnitude of the gradient can be reduced by accepting the direction of the gradient as any of the above three possibilities, and then performing additional scanning steps along this gradient direction at points at distances rn from the first location (x1,y1). The points at rn distances can be equally spaced on the ray connecting the first location at (x1,y1) and the point on the loop corresponding to $z_{max}$, or selected by some other criterion. Labeling the newly scanned z values on the ray connecting the first location at (x1,y1) and the point on the loop corresponding to $z_{max}$ as $z_{max}(r1), z_{max}(r2), z_{max}(rn)$ and the newly scanned values on the ray connecting (x1,y1) and the point on the loop corresponding to $z_{min}$ as $z_{min}(r1'), z_{min}(r2'), \ldots z_{min}(rn')$, approximations of the magnitude of the gradient can be obtained by various implementations:

$$|\vec{\nabla} z(x1,y1)|(n) \approx (z_{max}(rn)-z(x1,y1))/rn; \text{ or} \qquad (i')$$

$$|\vec{\nabla} z(x1,y1)|(n) \approx (z(x1,y1)-z_{min}(rn'))/rn'; \text{ or} \qquad (ii')$$

$$|\vec{\nabla} z(x1,y1)|(n) \approx (z_{max}(rn)-z_{min}(rn'))/(rn+rn').$$

Any of these three implementations can then proceed by averaging over N of these discrete differentials:

$$\langle |\vec{\nabla} z(x1, y1)| \rangle = \frac{1}{N} \sum_{n=1}^{N} |\vec{\nabla} z(x1, y1)|(n), \qquad (iv')$$

to obtain the magnitude of the gradient with improved precision and reduced noise. Some methods may mix the above implementations. These averaging methods can determine the magnitude of the gradient with increasing accuracy for increasing N. Other noise-reduction methods can be used as well.

Returning to FIG. 3A, in step 130 a second location can be selected by shifting the first location—in the illustrated case the initial location (x1,y1)—by an increment vector 114-1 along the direction of the gradient. The magnitude of the increment vector 114-1 can be proportional to the magnitude of the gradient, such as the magnitude times the step-size-control parameter $\gamma$.

In some implementations where the direction of the increment or update vector may not be entirely parallel to the gradient, but can be related to it. The increment vector can make a predetermined angle with the gradient vector, or it can be offset from the gradient's direction by a random angle.

Figure 4:
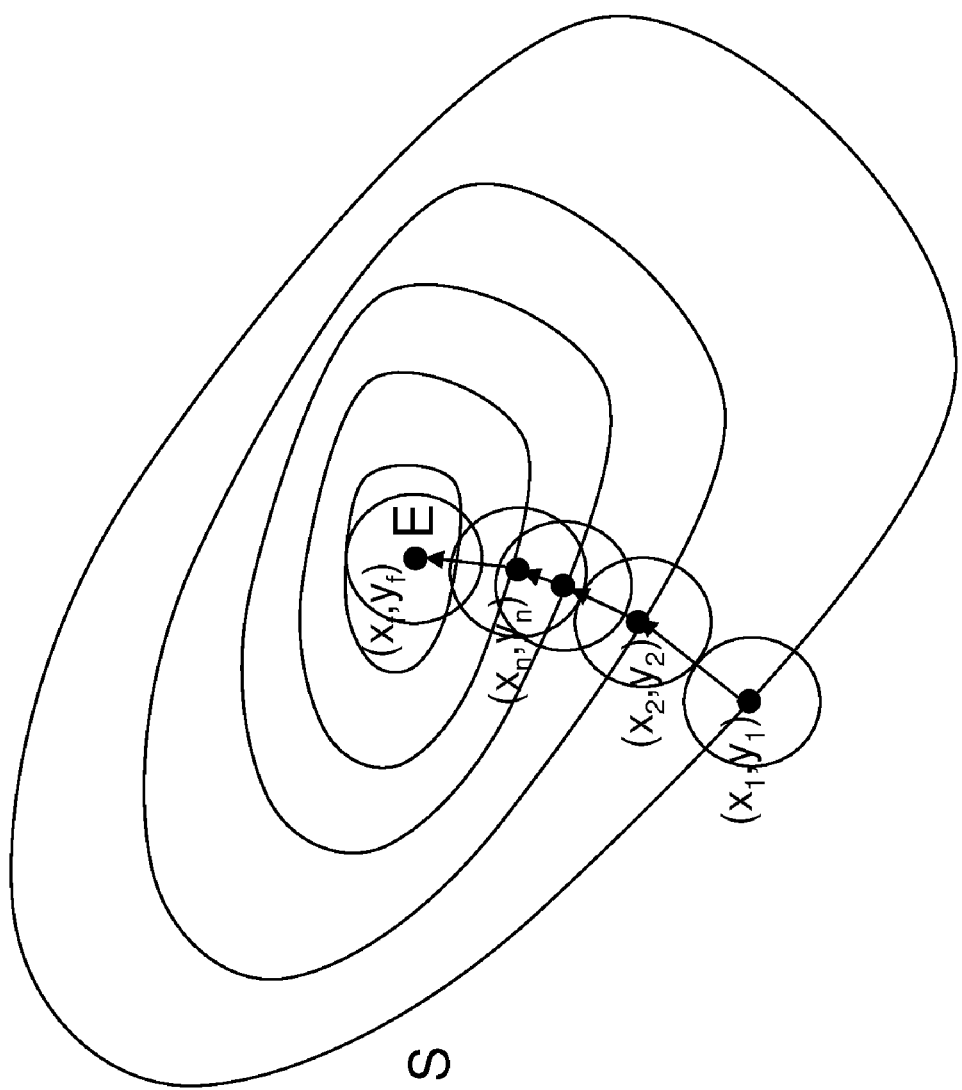
FIG. 4 illustrates the iterative aspect of the gradient search algorithm.

FIG. 4 illustrates that steps 110-130 can be performed repeatedly, incrementing the locations (xn,yn) progressing towards the final location (xf,yf), where the coordinate z assumes its maximum value: $z(xf,yf)=z(Max)$. Note that $z_{max}$ denotes the maximum of the coordinate along the individual search loops corresponding to a specific location, whereas $z(Max)$ denotes the overall maximum of the $z=z(x,y)$ surface being searched.

The magnitude of the increment vectors 114-n, also called the step size, can be proportional to the magnitude of the gradient vector. The constant of proportionality, $\gamma$ can be the same for all steps, or it can vary step-by-step: $\gamma=\gamma(n)$. The other parameters, such as the radius of the loop r, can be also selected by a user of the method 100, or by a controller computer, and can either remain the same or vary step-by-step. These parameters of the method 100 can be selected in order to achieve a fast convergence of the method 100. The parameter selection can depend on the steepness of the gradient, the complexity of the surface and the loop, the desired accuracy, the measurement noise and other considerations.

The GSILI method 100 can be terminated when a magnitude of the gradient is smaller than an iteration-stop value. In some cases the magnitude of the increment vector can be reduced gradually to avoid overshooting or getting into an oscillating or circulating cycle. In practice, when the increase of the z coordinate becomes smaller than a first value, then $\gamma$ can be reduced to a $\gamma1 < \gamma$ value when continuing the method. This gradual reduction step can be repeated to increase precision.

Figure 5:
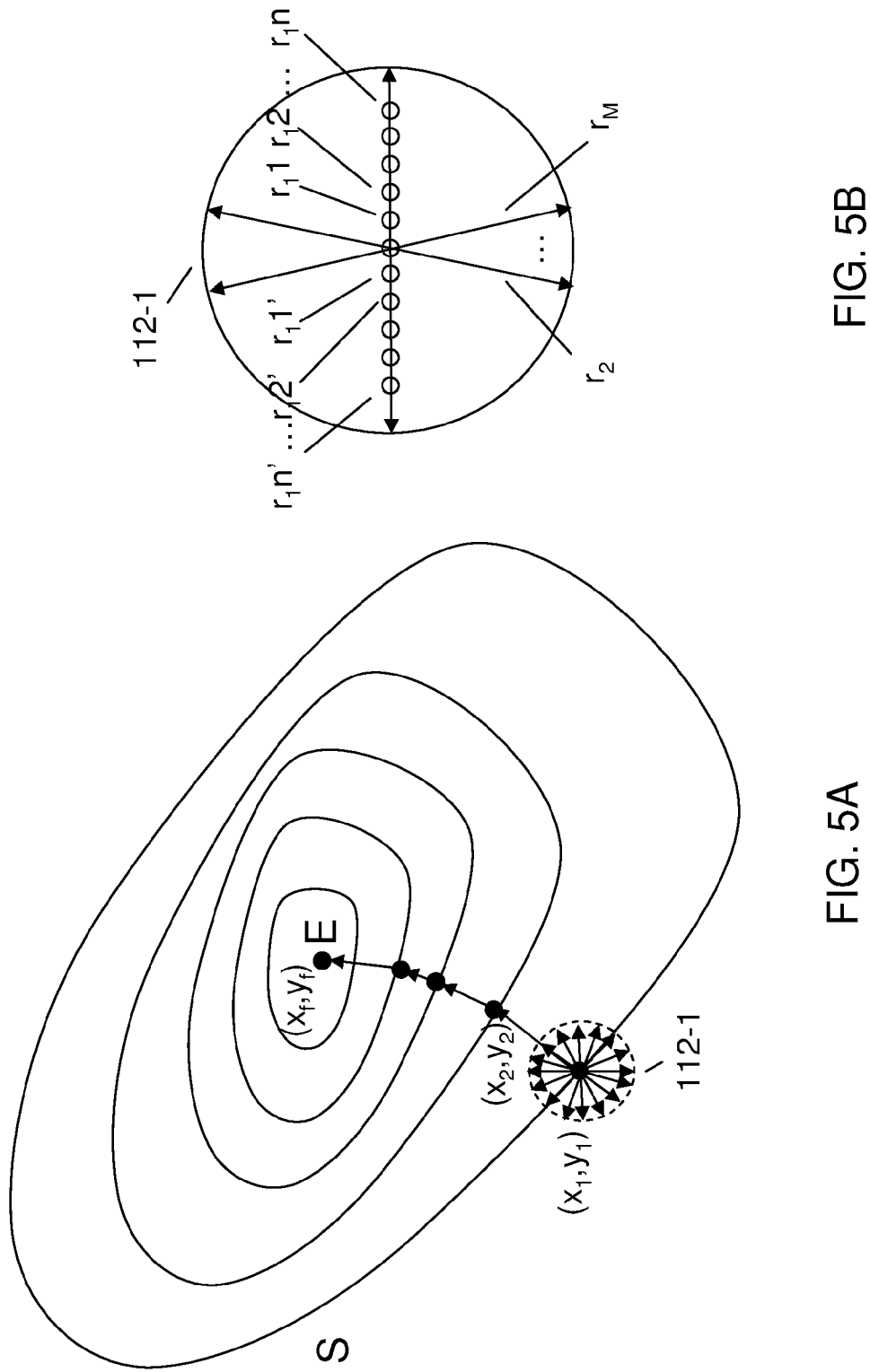
FIGS. 5A-B illustrate a ray-based local search step.

FIGS. 5A-B illustrate another embodiment of step 110.

FIG. 5A shows that the coordinate z can be also determined "in relation to the loop" in the sense that the coordinate z is determined along rays, emanating from the first location and ending on or nearby the loop 112-1. Taking the gradient is a numerical derivation and can produce noisy results, possibly with low precision. This noise could lead to an imprecise determination of the direction and magnitude of the gradient. The averaging implementations (i')-(iv') above reduce the noise in the magnitude of the gradient, but still use only two points regarding the direction. Thus the direction of the gradient is determined only with a limited accuracy by the method 100.

FIG. 5B illustrates that this implementation can include the steps of:

(a) identifying several ray directions 1, ... M (only rays 1, 2, and M are shown for clarity);

(b) determining the value of the z coordinate at points on the first ray at: $r_1 1, r_1 2, \ldots r_1 n$ and $r_1 1', r_1 2', \ldots r_1 n'$, up to points on the M-th ray at $r_M 1, r_m 2, \ldots r_m n$ and $r_m 1', r_M 2', \ldots r_m n'$, where n can assume values up to N and n' up to N';

(c) determining the rate of change along the M rays by any of the averaging methods (i')-(iv');

(d) selecting the ray along which the rate of change is maximum; and (e) identifying the direction of the selected ray as the direction of the gradient, and the rate of change along the selected ray as the magnitude of the gradient.

In these implementations the number of ray-points N can be between 1 and 100, in some cases between 1 and 10, and the number of rays M can be between 1 and 100, in some cases between 1 and 10.

For relatively smooth and differentiable surfaces the GSILI method 100 converges to a local extremum of the boundary of the imaged region. However, it is possible that the searched boundary has more than one extrema, only one of them being the global or overall extremum. However, the GSILI method 100 can very well get trapped in any one of the local minima. At the same time, some implementations of the GSILI method 100 are directed towards determining the global extremum of the boundary, and thus the search getting trapped in a local minimum poses a challenge.

In addition, if the imaging returns the z coordinates with lower precision, the corresponding noise may create lots of shallow apparent minima, again capable of trapping the search algorithm 100, in analogy e.g. to glassy problems in scientific applications.

To overcome these two types of trapping, implementations of the GSLI method 100 can be supplemented with known variations developed for optimization methods. Some optimization methods avoid the search getting trapped in a local minimum by applying occasional random jumps not controlled by the local gradient.

These random-jump implementations can shift, or update the location (xn,yn) by a shake-up vector, whose direction is not parallel with the direction of the gradient. The magnitude of the shake-up vector can be chosen to be sufficiently large to move the search out of the basin of attraction of the local minimum. In other embodiments, the direction of the shake-up vector can be related to the direction of the gradient, but the magnitude of the shake-up vector can be considerably different from the magnitude of the gradient.

Returning to the overall merits of the GSILI method 100, the search method 100 can be performed without performing the grid-scan of FIG. 1B, or equivalently, without determining the coordinate of the boundary of the region in one of a volume, along parallel lines, in a two dimensional raster or grid, and in a raster on a surface. For this reason, the GSILI method 100 can be performed in a valuably short time.

In ophthalmic applications the imaged boundary of a region can be the ophthalmic layer of one of a cornea, a lens, and a cataract; the coordinate can be a depth of the ophthalmic layer; and the search method 100 can be directed to determine an extremum of the ophthalmic layer.

Since the GSILI method 100 performs local searches instead of grid scanning the entire target region, it can be performed considerably faster. In the above ophthalmic implementation the search method 100 is capable of determining an extremum of the ophthalmic layer faster than one of 10 msec, 100 msec, 1 sec and 10 sec. Given that ophthalmic patients often experience difficulties keeping their eyes under control past 90-120 seconds, and given the time constraints of the entire surgical procedure itself, the total time of the search method being below 10 sec can allow an in-situ identification of a reference point on an ophthalmic layer as an introductory phase of the surgery. If the search method can be performed below 1 sec, then it can be performed repeatedly during the ophthalmic procedure, providing feedback about its progress. If the search method can be performed below 100 msec, then a limited resolution near-real time imaging of a reference point may be possible, and if the method can be performed below 10 msec, then a good resolution near-real time imaging of a reference point may be possible.

Figure 6:
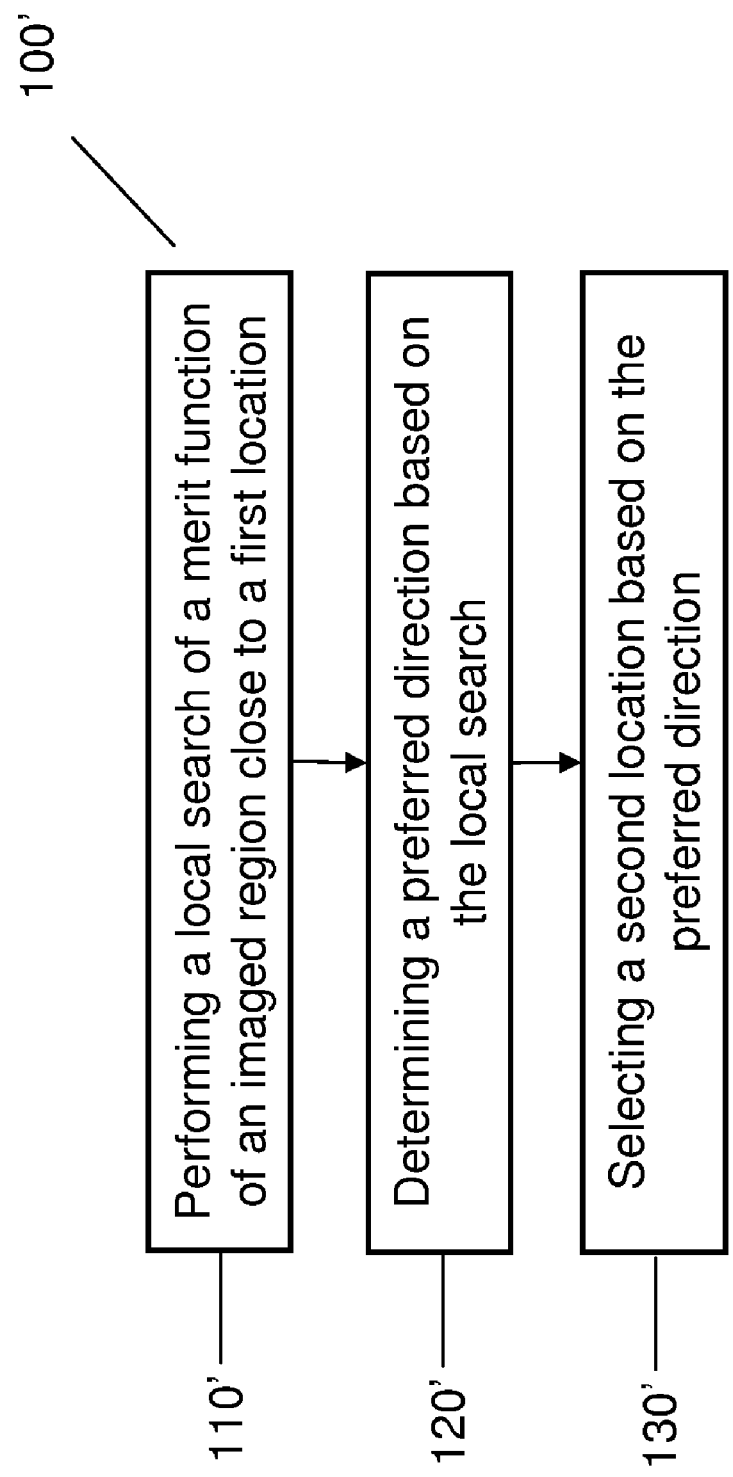
FIG. 6 illustrates a search algorithm based on a local search of a merit function 100'.

FIG. 6 illustrates yet another embodiment 100' of the search method, possibly in a surgical context, including: performing a local search of a merit function of an imaged region in the proximity of a first location in step 110'; determining a preferred direction based on the local search in step 120'; and selecting a second location based on the preferred direction in step 130.

In FIG. 6, the local search in step 110' can include imaging by one of an optical coherence tomography, a depth measurement technology, an optical sensing technology and a sensing technology of the merit function.

The merit function can be any spatial coordinate, a height, a depth, a surface z coordinate, any optical property, such as a scattering strength, a reflectivity, a transmittivity, an absorptivity, any of the above properties in any portion of the electromagnetic spectrum, such as in the infrared or ultraviolet portion, and any mechanical property. In other implementations, the merit function can be a combination of sensed quantities, e.g. the product or weighted sum of an optical reflectivity and an ultraviolet scattering strength. A large number of composite merit functions are possible, combining various performance parameters.

Any of these merit functions can be imaged if the merit function exhibits a detectable variation across the target layer.

An example is the optical scattering strength exhibiting a rapid increase when the cataract region is reached during the scan of the nucleus.

The local search step 110' can include searching in two or three dimensions in the proximity of the first location. Correspondingly, the merit function can be determined along a closed loop, a loop in a plane, a loop on a predetermined surface, an ellipse, a circle, an essentially closed surface, an ellipsoid, and a sphere, as well as along local rays.

In step 120' the preferred direction can be determined as a direction of a gradient of the merit function.

Analogously to method 100 in FIG. 2, the direction of the gradient in FIG. 6 can include determining at least one of a location of a maximum of the merit function on an essentially closed surface or loop around the first location, and a location of a minimum of the merit function on the essentially closed surface or loop around the first location, followed by determining the direction of the gradient by relating any two of the first location, the location of the maximum and the location of the minimum. Any of the above methods can be applied to determine the gradient, including the various averaging methods.

Once the direction and magnitude of the gradient is determined, in step 130' the selecting a second location step can include selecting the second location by shifting the first location by an increment vector, where a direction of the increment vector can be essentially parallel to the direction of the gradient.

After the steps 110'-130' have been repeatedly performed, the search method 100' can be stopped when the magnitude of the gradient becomes smaller than an iteration-stop value, since this signals that the method 100' reached the immediate vicinity of the sought extremum.

Since the method 100' performs the searches only locally, it does not involve determining the merit function of the imaged region in a volume, along parallel lines, on aligned surfaces, and in a two or three dimensional raster or grid.

Figure 7:
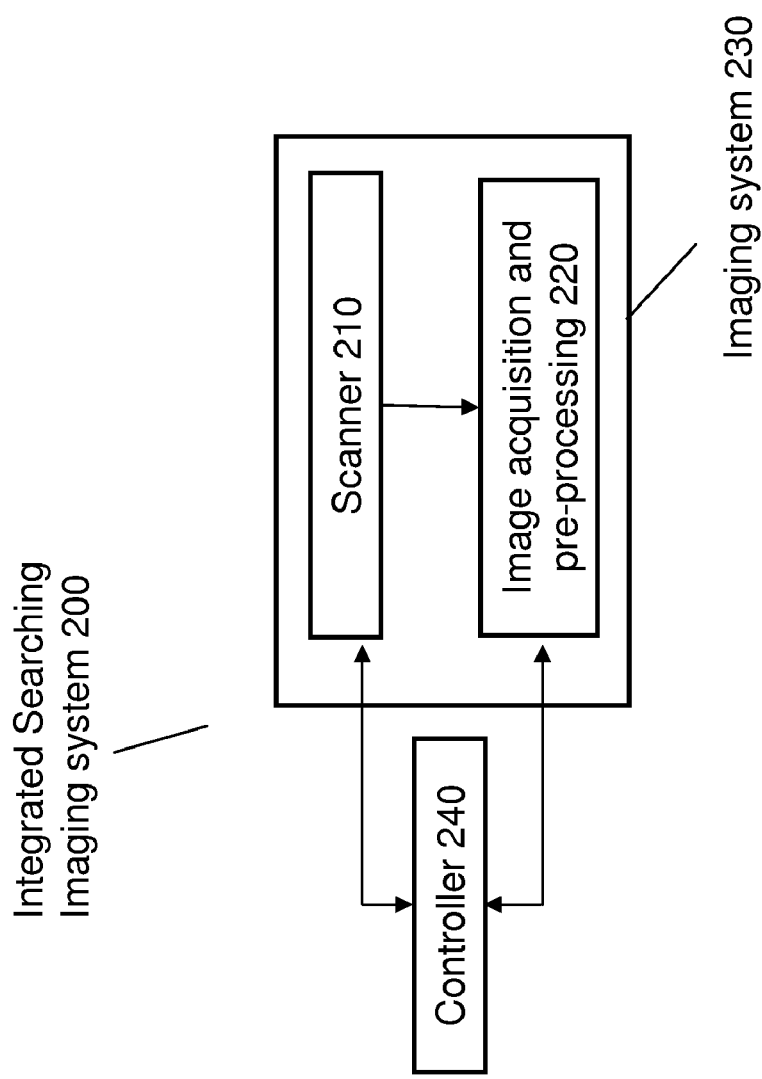
FIG. 7 illustrates an integrated searching and imaging system 200.

FIG. 7 illustrates an Integrated Searching-Imaging (ISI) system 200. The ISI system 200 is capable of performing the methods 100 or 100'. The ISI system 200 can include a scanner 210 and an image acquisition and pre-processing unit 220, both being part of the imaging system 230. The scanner 210 is configured to scan a laser imaging beam in an imaged region. The image acquisition and pre-processing unit 220 can receive and pre-process a returned imaging beam. In implementations, the imaging system 230 can be configured in various forms, e.g., an optical coherence tomography system, a depth measurement system, or a sensing system of a merit function.

The imaging system 230 is capable of determining a coordinate of a feature of an object or a boundary of a region. The imaging process can be based on sensing any optical or mechanical property exhibiting a detectable change at the boundary.

A controller 240 is provided to control the scanner 210 and the image acquisition and pre-processing system 220. The communication between these subsystems can be bi-directional. The controller 240 can direct the imaging system 230:

(i) to determine the coordinate in a loop in the proximity of a first location;

(ii) to determine a direction of a gradient of the coordinate corresponding to the first location; and (iii) to select a second location based on the determined direction.

The controller 240 can be configured to determine at least one of a location of a maximum of the coordinate along the loop and a location of a minimum of the coordinate along the loop, and to determine the direction of the gradient by relating any two of the first location, the location of the maximum and the location of the minimum.

The controller 240 can further select the second location by shifting the first location by an increment vector, where the direction of the increment vector can be essentially parallel to the direction of the gradient.

The controller 240 can be also configured to stop the search when a magnitude of the gradient becomes smaller than an iteration-stop value.

In ophthalmic implementations, the imaging system 230 can be an ophthalmic coherence tomography system; the imaged boundary of a region can be an ophthalmic layer of a cornea, a lens or a cataract, and the coordinate can be a depth of the ophthalmic layer. The scanner 210 can move a focal spot of an imaging beam along a loop in a surface, such as an (x,y) plane. The image acquisition system 220 can sense the returned portion of the imaging beam e.g., by a sensor or array of sensors to determine a coordinate of the imaged boundary, such as its z depth. In these implementations the controller 240 can be configured to determine an extremum of the ophthalmic layer.

In such ophthalmic applications the ISI system 200 can determine the extremum of the ophthalmic layer faster than one of 10 msec, 100 msec, 1 sec and 10 sec. Each of these values is associated with a unique functionality, as described earlier.

As repeatedly stated earlier, while some aspects of the implementations of the methods 100 and 100' were described in relation to surgical procedures, these methods are equally applicable in any situation when the imaging of an entire surface or boundary is not needed, only the identification of their extrema or boundaries or some other features. As such, the methods 100 and 100' can be applied for any material machining, diagnostic, quality control, and manufacturing applications.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

A number of implementations of image-guided laser surgical techniques, apparatus and systems have been disclosed. However, variations and enhancements of the described implementations and other implementations can be made based on what has been described.

The invention claimed is:

1. A method for searching a gradient of a function over a target object, comprising:

selecting a first location of the target object;

performing a sensing or measuring operation at the first location to obtain a respective value of the function;

selecting a first loop having multiple first loop locations of the target object that are different from the first location;

performing a sensing or measuring operation at the multiple first loop locations of the first loop, without performing the sensing or measuring operation at other locations, to obtain values of the function at the respective multiple first loop locations;

selecting one of the multiple first loop locations that has the maximum or minimum value for the function among the multiple first locations;

using the first location and the selected first loop location that has the maximum or minimum value for the function among the multiple first loop locations, and corresponding values of the function to determine a first gradient between the first location and the selected first loop location;

selecting a second location of the target object along a direction of the first gradient;

performing a sensing or measuring operation at the second location to obtain a respective value of the function;

selecting a second loop having multiple second loop locations of the target object that are different from the second location;

performing a sensing or measuring operation at the multiple second loop locations, without performing the sensing or measuring operation at other locations, to obtain values of the function at the respective multiple second loop locations;

selecting one of the multiple second loop locations that has the maximum or minimum value for the function among the multiple second locations; and using the second location and the selected second loop location that has the maximum or minimum value for the function among the multiple secondt loop locations, and corresponding values of the function to determine a second gradient between the second location and the selected second loop location;

wherein the sensing or measuring operation at a location of the target object to obtain a respective value of the function includes optically imaging the location of the target object to obtain information regarding the respective value of the function;

wherein the target object is a target tissue of a patient and the function is a function of a height, depth or thickness of the target tissue with respect to location;

wherein the steps of the method performed each comprise an operation of a controller and an imaging system coupled to the controller.

2. The method of claim 1, wherein the first loop is a closed loop that surrounds the first location.

3. The method of claim 1, wherein the first loop is a closed loop and the first location is outside the first loop.

4. The method of claim 1, wherein the first loop has one or more discontinuities.

5. The method of claim 1, wherein the sensing or measuring operation at a location of the target object to obtain a respective value of the function includes measuring a temperature at the location of the target object.

6. The method of claim 1, wherein the sensing or measuring operation at a location of the target object to obtain a respective value of the function includes measuring an optical refractive property at the location of the target object.

7. The method of claim 1, wherein the sensing or measuring operation at a location of the target object to obtain a respective value of the function includes measuring a density at the location of the target object.

* * * * *